(12) United States Patent
Tata

(10) Patent No.: US 6,964,191 B1
(45) Date of Patent: Nov. 15, 2005

(54) APPARATUS AND TECHNIQUE FOR MEASURING PERMEABILITY AND PERMEANT SORPTION

(76) Inventor: Murthy Tata, 534 W. Hemlock Way, Chandler, AZ (US) 85248

( * ) Notice: Subject to any disclaimer, the term of this patent is extended or adjusted under 35 U.S.C. 154(b) by 0 days.

(21) Appl. No.: 10/685,321

(22) Filed: Oct. 14, 2003

Related U.S. Application Data

(60) Provisional application No. 60/418,444, filed on Oct. 15, 2002.

(51) Int. Cl.[7] .......................................... G01N 15/08
(52) U.S. Cl. ............................ 73/38; 73/40.7; 73/49.3
(58) Field of Search .......................... 73/38, 40.7, 49.2, 73/49.3

(56) References Cited

U.S. PATENT DOCUMENTS

| | | | |
|---|---|---|---|
| 3,850,040 A * | 11/1974 | Orr et al. .................... | 73/865.5 |
| 4,047,422 A * | 9/1977 | Lyssy .............................. | 73/38 |
| 4,944,180 A * | 7/1990 | Tou et al. ....................... | 73/38 |
| 5,002,399 A * | 3/1991 | Akinc et al. ................... | 374/14 |
| 5,138,871 A * | 8/1992 | Retta et al. ..................... | 73/38 |
| 5,239,482 A * | 8/1993 | Ajot et al. ..................... | 702/30 |
| 5,345,814 A * | 9/1994 | Cur et al. ..................... | 73/49.3 |
| 5,580,925 A * | 12/1996 | Iwahara et al. ............. | 525/100 |
| 6,327,892 B1 * | 12/2001 | Koiso et al. .................... | 73/38 |
| 6,450,012 B1 * | 9/2002 | Mayer et al. ................ | 73/49.3 |
| 6,460,405 B1 * | 10/2002 | Mayer et al. ................ | 73/40.7 |
| 6,477,888 B1 * | 11/2002 | Mizobe ......................... | 73/38 |
| 6,598,463 B2 * | 7/2003 | Sharp et al. .................... | 73/38 |
| 2002/0194899 A1 | 12/2002 | Gebele et al. | |

* cited by examiner

*Primary Examiner*—John E. Chapman
*Assistant Examiner*—John Fitzgerald
(74) *Attorney, Agent, or Firm*—Parsons & Goltry; Robert A. Parsons; Michael W. Goltry

(57) ABSTRACT

The invention is concerned with apparatus and methods for measuring package permeability and/or permeant sorption. The apparatus includes a housing defining an inner sealed chamber that is substantially impervious to a permeant of interest. The chamber has an inlet for introducing an inert medium substantially free of the permeant and an outlet for removing the inert medium. A sensor is positioned within the chamber and to provide signals indicative of permeant concentrations. A sealable opening is provided in the housing for introducing, within the chamber, packages to be measured for permeability and/or permeant sorption. In the method, testing of permeant concentrations is cycled to determine the slope of a time line between a low and a high concentration of the permeant. Humidity and temperature are preferably maintained constant within the chamber during testing.

11 Claims, 6 Drawing Sheets

APPARATUS AND TECHNIQUE FOR MEASURING PERMEABILITY AND PERMEANT SORPTION

CROSS-REFERENCE TO RELATED APPLICATIONS

This application claims the benefit of U.S. Provisional Application No. 60/418,444, filed 15 Oct. 2002.

FIELD OF THE INVENTION

The invention relates to measuring material permeability characteristics.

More specifically, it relates to measuring gas or vapor diffusion through packaging materials.

Even more specifically, it relates to measuring the flux of CO2 through bottles and films such as those used for packaging carbonated beverages.

BACKGROUND OF THE INVENTION

Plastics materials are increasingly being used in packaging applications, replacing glass and metal. However, plastic materials generally have inferior vapor barrier properties compared to glass and metal containers. Accordingly, plastic packages generally admit oxygen into the package at a faster rate, show higher aroma loss, higher water vapor loss, and greater $CO_2$ loss in case of carbonated beverage packages. Other advantages afforded by plastics such as lighter weight, lower cost, the ability to form attractive container shapes continues to sustain or increase the share of plastics in packaging applications. Improved test methods are therefore constantly being developed to measure plastics barrier properties.

When the permeant of interest is $CO_2$, for example, in measuring shelf life of carbonated beverage packages, two broad categories of methods are presently used. The first methods measure retained $CO_2$ in the packages by periodically measuring $CO_2$ in a simulated shelf-life test. The second methods measure the rate of $CO_2$ loss from the package at a point in time and at a measured driving force (partial pressure) in the container. For typical packages of interest, methods measuring retained $CO_2$ have several deficiencies. The $CO_2$ content changes only very slightly (10 to 15%) during the shelf life, demanding exquisite sensitivity in the detection mechanism because one is required to measure such small changes over a large offset. In addition, such small signal changes occur over very long periods of time (8 to 12 weeks—essentially the expected shelf life of the package) rendering these methods useless for rapid permeation assessment. As such, these methods are of little predictive value. The $CO_2$ loss rate measurement methods, which in principle can measure the signal without having to measure against a large offset as in the retained $CO_2$ methods, in their current implementation have several disadvantages as discussed below. Although loss rate methods are faster than the retained $CO_2$ methods, they are often inaccurate and shelf life predictions from such methods often do not concur with measurements using the retained $CO_2$ tests. The present invention overcomes deficiencies of the loss rate measurement methods in prior art and thus provides a method that is not only very rapid, but also predicts shelf life with accuracy.

Several techniques and apparatus for measuring oxygen permeability of plastic films are patented and published. Usually, the film sample of interest is sandwiched between two test chambers using appropriate sealing mechanisms. One chamber is exposed to the permeant gas of interest in high concentrations while the second chamber is purged continuously with an inert carrier gas. Any permeated permeant from the first chamber is thus transported to a permeant detector located outside these permeation chambers. The detector itself is usually a sensor that is capable of measuring extremely small concentrations of the permeant. While in principle the method can also be applied to testing containers, such a configuration does not lend itself to nondestructive testing of whole containers.

Use of such a continuous purging system is also disadvantageous for other reasons. The concentration of permeated permeant is often extremely small in the second chamber, especially when the sample material is a good barrier. Measuring such low concentrations of the permeants reliably is a challenge for most sensors. Furthermore, such low permeant concentrations are diluted several fold when a carrier gas is used to transport the permeated permeant to the remote detector. The objective of the measurement, the true permeation rate is directly related to the product of carrier gas flow rate and the detector response. For accurate estimation of permeation rates, it becomes essential that the flow rate of the carrier gas be accurately and robustly controlled, and also that the detector be capable of exquisite sensitivity.

In addition, the permeability of many barrier materials is highly sensitive to temperature and humidity conditions at the time of the test. For example, $CO_2$ permeability of EVAL-F, a commercially available barrier material, increases about 30-fold when the relative humidity increases from 50% to 90%. Most beverage packages contain 100% relative humidity inside the package. It is of interest to measure permeability under precisely defined high external humidity conditions. To my knowledge, the relevant prior art does not teach how testing at precisely controlled high relative humidities is to be conducted. Precise control of humidity, especially at high humidity levels is difficult to achieve in current systems mainly because of the difficulty associated with controlling humidity in a continuous purge stream. Further, humidity control in the first chamber, where the permeant source is provided is even more difficult, and is left uncontrolled.

An example of non-flowing systems used for package permeability testing is described in U.S. patent application U.S. 20020194899A1 published Dec. 26, 2002, titled "Method and Device for the Determination of the Gas Permeability of a Container" (equivalent world patent WO 0148452). Here, packages containing high partial pressures of the permeant are placed in a confinement chamber in such a way as to minimize the spacing between the package and the chamber. As the permeant permeates to this inter-space, the pressure therein increases and is measured with a sensitive pressure gage. The disadvantage with such a system is that plastic containers expand under pressure. Thus, the volume of the inter-space can change significantly causing erroneous pressure readings. Thus, while this method could be faster than the retained $CO_2$ methods, its practical utility is limited to measuring relative barrier property differences between different packages rather than absolute permeability measurements for each package independently that is necessary for shelf life predictions. Further, since the method relies heavily on minimizing the volume of the inter-space between the given confining chamber and the package, significant deviations in the test package shape or size will require completely different chambers to be used. Lastly, methods for accurate humidity control that are critical for most barrier property testing are not taught in the above described U.S. patent application.

Another example of a non-flowing system used in the field of vacuum insulation panel testing is described in U.S. Pat. No. 5,345,814, issued 13 Sep. 1994, and entitled "Method and Apparatus for Testing Vacuum Insulation Panel Quality". Vacuum insulation panels are prepared by evacuating air and introducing small quantities of helium tracer gas into the panels just prior to sealing. The panels are placed in an evacuated chamber at an even lower pressure than within the panels and the helium is allowed to flow out of the insulation panel into the chamber space. The integrity of the panels is assessed by sampling the chamber gases to measure the rate of helium accumulation. While this approach overcomes some of the limitations of the continuous purge systems, it uses a flow or a sniffer type detector, and relies on the contents of the chamber to be exhausted with an elaborate equipment set up. Most critically, the '814 patent does not teach ways of temperature and humidity control in package testing.

Further, no prior art references teach a method for measuring sorption of the permeant by the packaging materials empirically.

It would be highly advantageous, therefore, to remedy the foregoing and other deficiencies inherent in the prior art.

Accordingly, it is an object of the present invention to provide new and improved apparatus and techniques for measuring package permeability.

Another object of the invention is to provide new and improved apparatus and techniques for measuring package permeant sorption.

Another object of the invention is to provide new and improved package permeability measuring apparatus and techniques that are extremely accurate.

Another object of the invention is to provide new and improved package permeability measuring apparatus and techniques that are substantially faster than prior art apparatus and techniques.

A further object of the invention is to provide new and improved package permeability measuring apparatus and techniques that can be used on substantially any types, shapes, and sizes of packages.

A further object of the invention is to provide new and improved apparatus and techniques for measuring package permeant sorption wherein accurate control of humidity and temperature are better achieved.

SUMMARY OF THE INVENTION

Briefly, to achieve the desired objects of the instant invention in accordance with a preferred embodiment thereof, apparatus and methods for measuring package permeability and/or permeant sorption are disclosed. The apparatus includes a housing defining a sealed chamber that is substantially impervious to the permeant of interest. The chamber has an inlet for introducing an inert medium substantially free of the permeant and an outlet for removing the inert medium. A sensor is positioned within the chamber to provide signals indicative of permeant concentrations within the chamber. A sealable opening is provided in the housing so that packages, to be measured for permeability and/or permeant sorption, can be introduced within the chamber. In the method, testing of permeant concentrations is cycled to determine the slope of a time line between a low and a high concentration of the permeant. Humidity and temperature are preferably maintained constant within the chamber during testing.

Accurate and precise humidity controlling apparatus is also disclosed. The humidity controlling apparatus includes a bag or package formed of microporous hydrophobic material, such as GORTEX™, or Celgard 2500™. The bag or package contains a saturated salt solution together with some excess undissolved salt specifically selected to maintain a desired humidity within the chamber. The size of the bag and the amount and type of salt solution contained therein is pre-calculated to maintain the selected humidity in the chamber or other closed area.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

DETAILED DESCRIPTION OF THE PREFERRED EMBODIMENTS

Figure 1:
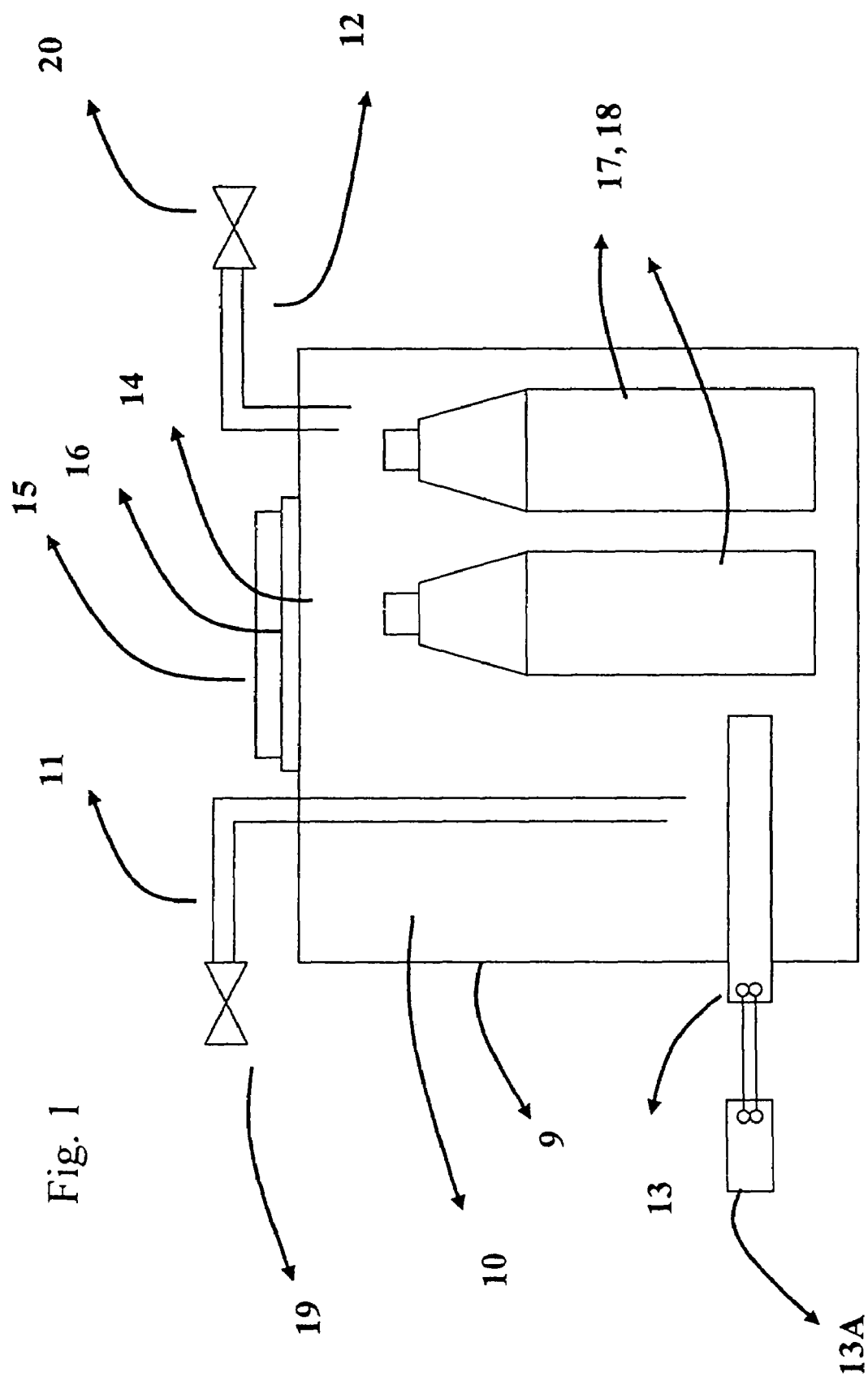
FIG. 1 is a semi-schematic diagram illustrating testing apparatus and a method of apparatus set-up in accordance with the present invention.

Turning now to the drawings in which like reference characters indicate corresponding elements, attention is first directed to FIG. 1 which illustrates a housing 9 defining an inner sealed chamber 10 with several attachments. Housing 9 and all the attachments are preferably made of materials substantially impervious to the permeant of interest, for example, stainless steel. Tubings 11 and 12, connected to an inlet and an outlet, respectively, of chamber 10, are used to flush chamber 10 with an inert medium. A valve 19 connected to tubing 11 and a valve 20 connected to tubing 12 are included for this purpose. A permeant sensor 13 is conveniently located at least partially within chamber 10 so that permeant within chamber 10 can be sensed and noted externally of chamber 10. The inert medium, which is also substantially free of the permeant, is chosen such that it does not interfere with the detection of permeant by permeant sensor 13.

For example, if carbon dioxide ($CO_2$) is the permeant of interest, one could use nitrogen or air substantially free of $CO_2$ as the inert medium. Permeant sensor 13 is ideally located within the chamber to measure the changes in permeant concentration directly, as opposed to embodiments where a carrier gas transports the contents of chamber 10 to a sensor placed separate from chamber 10 but connected to chamber 10 by appropriate plumbing. Permeant sensor 13 is ideally based on the well known method of infrared radiation absorption for the permeants that significantly absorb at specific wavelengths in the infrared spectrum of electromagnetic radiation. However, any sensitive method of permeant quantification can be suitably chosen as applicable for the permeant of interest.

Chamber 10 has an opening 14 through which test samples, for example test samples 17 and 18, are introduced. A sealing cover 15 is removably connected over opening 14 and is sealed against opening 14 by an O-ring or a gasket type seal 16. Seal 16 is preferably made of formulations that exhibit low permeability for the permeant in question, for example, high-barrier elastomers and metallic seals. Following introduction of test samples 17 and 18 into chamber 10, opening 14 is closed and sealed by cover 15. Although only two test samples are depicted, it should be realized that any suitable number of samples that the container could accommodate could be used. Indeed, it is preferable to use as many test samples or packages as possible to shorten the test time. In this specific example, test samples 17 and 18 are bottles with appropriate closures, but any other choice of test samples or packages, filled with any substance that contains or generates a permeant of interest, can be tested.

The following example describes the application for measuring $CO_2$ permeation rates through plastic bottles, and sorption of $CO_2$ by such packaging materials. The plastic bottles, in this example test samples 17 and 18, are filled with a carbonated beverage or carbonated water at a known carbonation level, or simply with $CO_2$. The latter is conveniently achieved by weighing out appropriate amounts of dry ice and capping the bottle. Carbonated water could be prepared in the bottle by adding appropriate amounts of a carbonate or bicarbonate salt to a bottle filled with an aqueous medium, and adding a second reagent to decrease the pH of the medium below pH 5, most preferably, below pH 4.5 to insure liberation of substantially all the $CO_2$ from the bicarbonate. Alternately, a large batch of carbonated water could be simply filled into the packages using any filling device. If the carbonation level is not known prior to the start of the permeation test, it could also be determined by a suitable method after the test.

Test samples 17 and 18 are attemperated to the desired temperature at which the permeability is to be measured, preferably prior to introducing them into chamber 10. Most preferably, test samples 17 and 18 are prepared at the appropriate test temperature so no special attemperation step is required.

Once test samples 17 and 18 are introduced into chamber 10 and opening 14 is closed and sealed, valves 19 and 20 are opened, and chamber 10 is flushed, if necessary, with a suitable inert medium, for example, air. The inert medium is supplied to chamber 10 through valve 19 and tubing 11 while chamber 10 is vented through tubing 12 and valve 20. The volume of the inert medium used should be adequate to reduce the permeant concentration to suitably low levels, for example below the sensitivity (lowest accurately measurable permeant concentration) of permeant sensor 13. The inert medium could be appropriately preconditioned for the desired test conditions, for example temperature and relative humidity, before its entry into chamber 10. Following such a chamber flush, valves 19 and 20 are closed to completely isolate chamber 10 from the outside environment. $CO_2$ emitted by test samples 17 and 18 accumulates in chamber 10 and such increase in $CO_2$ concentration is measured by permeant sensor 13. In this preferred embodiment, signals from sensor 13 are recorded, externally, with a suitable device 13A to generate a history of permeant concentration over time.

Figure 2:
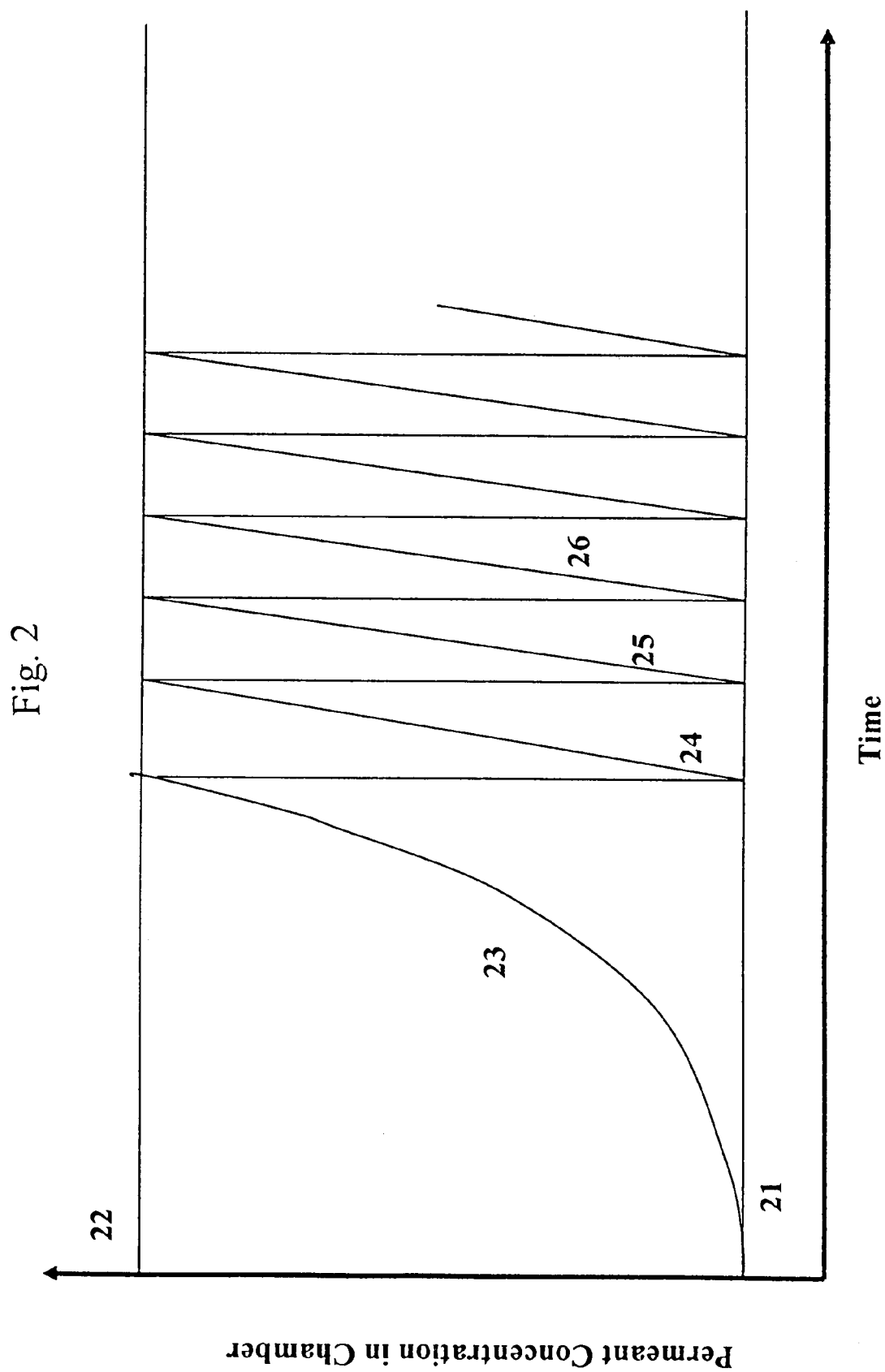
FIG. 2 is a graphical representation of an acquired signal in the apparatus set-up of FIG. 1, which acquired signal is further analyzed as described in the specification.

Attention is next drawn to FIG. 2, which is s graphical representation of typical permeant concentration history during a test in accordance with the present invention. If the package materials are relatively free of $CO_2$ (or the permeant in question) prior to packaging test samples 17 and 18 with carbonated substances, in this example, then steady state permeation is not established immediately in such packages. The rate of permeation through the packages and thus permeant accumulation rate in chamber 10 increases with time until a steady state is established whence it attains a substantially constant value. During the period of increasing permeation rates, shown as curve 23, the packaging materials absorb the permeant until they substantially saturate. Such a process of saturation is called henceforth "sorption" or "adsorption". Typically, it takes about 1 to 7 days for the sorption process to substantially complete. Until the sorption process is substantially complete, the permeation rate does not reach the steady state constant value. When the packages have been packaged significantly ahead of time, then such changes in permeation rates may not be readily apparent because permeation may have already substantially stabilized to the steady state permeation conditions. It must be noted that such time-dependent permeation rates are also seen whenever the test conditions (such as temperature, or humidity, or any other relevant test parameter) represent a deviation from those at which the package was equilibrated to prior to the test.

When the permeant concentration in chamber 10 increases to a suitably set high limit, designated 22 in FIG. 2, valves 19 and 20 are opened and chamber 10 is rapidly flushed with enough volume of the inert medium so as to reduce the permeant concentrations below a suitable low limit, designated 21 in FIG. 2. Suitable high limits are chosen such that the partial pressure of the permeant in chamber 10 is still substantially lower than that inside test samples 17 and 18 so that the accumulation of the permeant in chamber 10 would not significantly alter the permeation rate. Once low limit 21 is crossed, the inert medium flush is stopped, and valves 19 and 20 are closed to isolate chamber 10 and initiate another round of measurements.

Sensor signals can be continuously acquired through these recycling steps until the test procedure is stopped. The signal collected appears similar to that depicted in FIG. 2, where each cycle of chamber flush quickly decreases the chamber permeant concentration to low limit 21. While the first permeation cycle, e.g., 23, may show increasing permeation rates and nonlinear behavior, the monitoring of subsequent permeation steps produces progressively more linear accumulation profiles as shown in cycles 24, 25, and 26. Note that in FIG. 2, substantial nonlinear permeation is shown only in the first measurement cycle, it is possible to see significant nonlinearities in several of the subsequent measurement cycles depending on the actual test samples and the test conditions employed. The slope of each line segment in FIG. 2 increases gradually with each new cycle until steady state permeation is achieved when such slopes will remain substantially constant between successive cycles.

Instead of acquiring the sensor signal continuously, one may simply record the time intervals for the signal to reach the high limit from the low limit and thus calculate the rate of permeation into the chamber space. However, the slope of the sensor signal lines is better calculated by a linear regression of the collected sensor signal vs. time data because it allows for early estimation of the permeation rates without necessarily waiting till the concentration reaches the high limit setting. Further, it is advantageous to acquire the signal continuously when nonlinear behavior is to be analyzed, for example, when the objective is to determine the amount of $CO_2$ that the package adsorbs from a beverage. This application will be discussed later in this specification.

From the slopes of the sensor signal vs. time history (s) for each measurement cycle, one can calculate the rate of permeant loss R from each package by considering the total available chamber volume ($V_{ch}$), the total number of packages ($N_{pkg}$) (test samples 17, 18, etc.) placed in chamber 10, and the volume displaced by each package ($V_{pkg}$) thus:

$$R = \frac{s(V_{ch} - N_{pkg}V_{pkg})}{N_{pkg}} \quad \text{(eq. 1)}$$

The packages should be identically prepared such that each package is substantially the same as the rest in its initial permeant charge (driving force). The steady state permeation rate can be calculated by averaging the rates measured for several cycles after the steady state is achieved. Whether the steady state is attained could be determined by appropriate statistical test methods such as analysis of variance (ANOVA) and ensuring that an adequate number of measurement cycles are run to achieve the desired confidence level. Finally, average package permeability (P) is estimated by dividing the observed permeation rate (R) by the driving force partial pressure (p) or the permeant in the containers:

$$P = \frac{R}{p} \quad \text{(eq. 2)}$$

If the total amount of permeant in the packages is known at the beginning of the test, then one can estimate the time it takes for the loss of a fixed percentage of the permeant to occur. When measuring $CO_2$ loss from packages, typically the test can be completed in several minutes to several days depending on the barrier properties of the packaging materials and the history of the packages prior to the start of the test. Based on any arbitrary percentage loss tolerance specification (L) from an initial permeant charge ($C^0$), it is thus possible to predict accurately the retained permeant amounts at different times (C(t)) or shelf life (t) of the packaged product for several weeks or months hence using the following formulas:

$$C(t) = C^0 \cdot e^{-\left(\frac{PH}{V_L + \phi V_H}\right)t} \quad \text{(eq. 3)}$$

and $$t = -\left(\frac{V_L + \phi V_H}{PH}\right) \cdot \ln(1 - L) \quad \text{(eq. 4)}$$

where P is the permeability of the package (cc/pkg/d/atm), H is the solubility of the gaseous permeant in the liquid contained in the package (cc/atm), $V_L$ and $V_H$ are the volumes of liquid and headspace in the package (cc). $\phi$ is a correction factor to account for the fact that the headspace of the container is also a source for the permeant and is defined thus:

$$\phi = \frac{HT^*}{p^*T} \quad \text{(eq. 5)}$$

where T is the test temperature, and $p^*$ and $T^*$ are the pressure and temperature at which the volumes of permeant are referenced.

Figure 5:
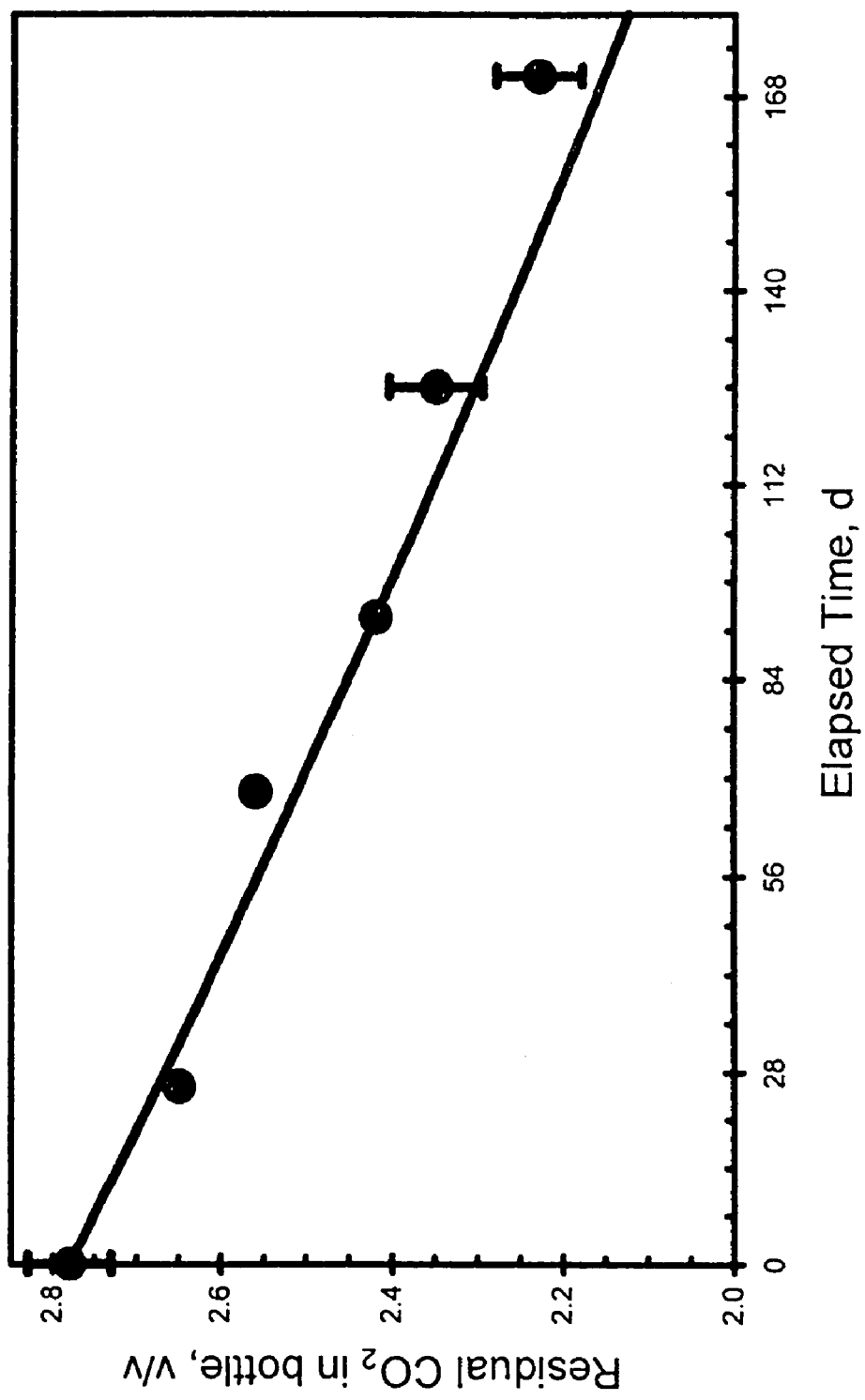
FIG. 5 illustrates a graphical representation of the results of a method performed in accordance with the present invention.

The advantages of the present invention will become evident upon examining FIG. 5. The subject packages of this graph were plastic barrier bottles packaged with carbonated water at conditions that allow packaging substantially free of air. They were then preconditioning at 75° F. and 75% relative humidity for 1 week in an environmental chamber to allow for bottle expansion under pressure ("creep") and $CO_2$ sorption to substantially complete and attain a steady state permeation regime. Although only 8 bottles were used for the permeation testing based on the current invention, many more were packaged in order to run a traditional long-term shelf life test for retained $CO_2$. The art of temperature and humidity control used here is disclosed later in this patent application.

Following 1 week of such preconditioning, 8 bottles were placed in the test chamber of the subject invention and the rate of $CO_2$ accumulation was measured with an infrared absorption sensor that is placed within the chamber. Room air was used as the inert medium and a set of 6 measurement cycles were conducted as described over a 3-day period. The driving force partial pressure of $CO_2$ in the packages was measured by measuring the pressure in each of the 8 packages tested and averaging over the eight measurements. Using equation (3) above, the retained $CO_2$ was thus estimated using the known driving force values as the initial permeant charge ($C^0$). The solid line of FIG. 5 represents charting of equation 3. The traditional long-term shelf life test was also conducted by periodically removing 3 to 5 bottles from the environmental chamber at different points into the shelf life for several months to measure retained $CO_2$ levels. The $CO_2$ content in the packages was measured by measuring pressure in the bottles using a piercing device (thus a destructive test). Average $CO_2$ content, together with error bars representing standard deviations for each measurement point are also plotted as symbols on FIG. 5.

It can be seen that the current method produces results that are in excellent agreement with the conventional shelf-life test that lasted over 6 months. Not only is the present test method of predictive value, it is also extremely rapid (3 days compared to 6 months for the traditional method). Further, since the test period is generally very short compared to typical package shelf live, the package loses only a negligible amount of the permeant, and thus the test can be considered nondestructive.

It must be noted that room air was used in this test method as a purge gas to clear the accumulated $CO_2$ in the test chamber between measurements. The room air had between 300 and 700 ppm of $CO_2$ contamination. In subsequent tests using nitrogen as the purge gas with negligible levels of $CO_2$ contamination, the same test could be completed within several hours because of improved signal discrimination from the background and when using linear regression for calculating the slopes or accumulation rates.

In addition to whole packages (e.g. test samples 17, 18), the technique could also be used to measure permeability of bottles or closures alone. For testing bottles, a suitable impervious liner could be used to seal the bottle. For example, aluminum foil seal liners could be used. When closures are of interest, an impervious bottle could be used in conjunction with the closure of interest. For example, stainless steel bottles with matching finish and the closure of interest could be use as a test package sample. The apparatus and technique could also be used when one is interested in measuring $CO_2$ evolution (and thus respiration rates) of biological samples and in testing materials that outgas specific compounds that could be detected by the sensor 13.

In plastic packages, often the closure members are made out of a different material (e.g. nylon or polypropylene caps with polyethylene or aluminum liners) than the container (e.g. polyethylene terepthalate or PET). Upon filling such packages with a product, if they are exposed to changes in temperatures (e.g., a bottle containing a beverage is chilled on ice), the different materials expand or contract differently because of differing thermal expansion coefficients, and could cause the closure to back-off or the seal to separate from the bottle finish affecting the gross package integrity. Accordingly, there is a need for rapidly assessing package integrity under conditions of temperature cycling. The current invention readily allows testing for package integrity under temperature cycling, i.e., varying temperature within chamber 10 during the measuring procedure according to a predetermined program to determine gross package integrity. For causing the package temperatures to change rapidly, the preferred method is to fill the bottles substantially fully with gaseous permeant (e.g. dry ice). If moisture is required for sealing performance, a small amount of water could be incorporated into the package. The test chamber temperature is varied according to a predetermined program and the sensor signal monitored continuously for sudden changes in permeant accumulation. The performance of the package seal is thus assessed under varying thermal loads.

The same methods can also be used to measure permeabilities of packaging films as follows. Attention is now drawn to FIG. 3, which is a simplified sectional view showing the makings of such a test package, designated 45. In this case, a test film 33 is mounted on a substantially impervious attachment 27 using O-rings 28 and 29. A screen 30 on the outside of test film 33 provides mechanical support and protects test film 33 from rupturing due to pressure variations thereacross. A retaining ring 31 fastens the film-screen assembly to attachment 27 by threaded connection. Alternative means of fastening the film-screen assembly to attachment 27, or similar structure can be employed (for example, TriClamp™ or other suitable flange clamping mechanisms) without deviating from the spirit of this invention. It is also possible to plumb the test chamber with a permeant source and provide for a mechanism of clamping the membrane directly to the inside of the test chamber. Attachment 27 is connected by another threaded connection or other suitable means to a container 32, which is also made of suitable impervious materials such as steel, aluminum, or glass.

Figure 3:
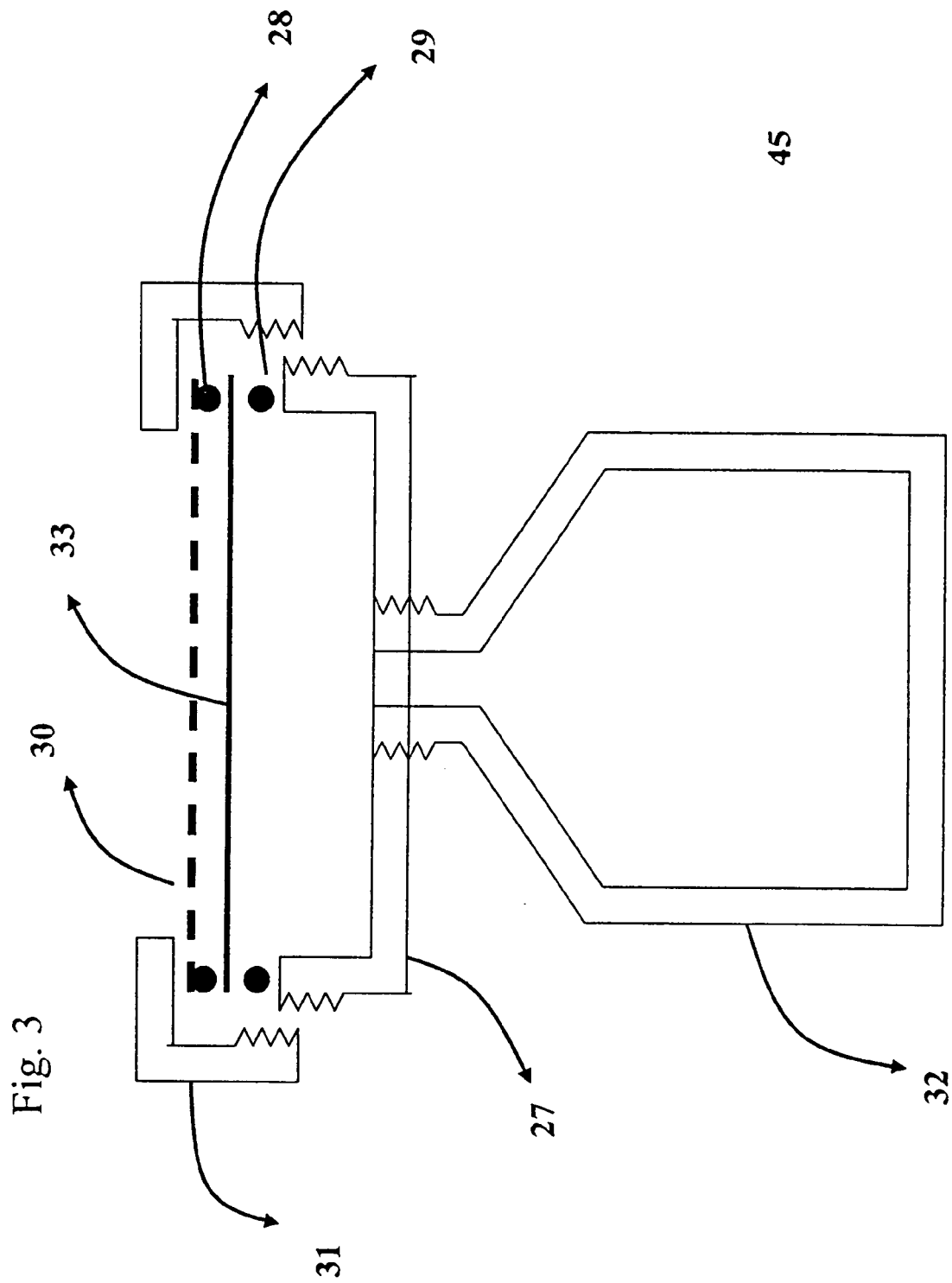
FIG. 3 is a simplified sectional view of a test package for measuring permeabilities of films in accordance with the present invention.

Container 32 contains a substance including the permeant or a substance that generates the permeant. Once one or more packages 45, such as those of FIG. 3, are assembled, a suitable number of them could be used in place of packages or test samples 17 and 18 of FIG. 1 to conduct permeation tests. When support screen 30 is employed, the measured permeation rate needs to be multiplied with a correction factor to account for the portion of the film area that is covered by the screen and is not active in permeation. Alternatively, standard test films whose permeability characteristics are known in advance could be tested with the screen and the ratio of the measured permeability to the known permeability could be used to determine such screen correction factors. When the support screen has a substantially open pore structure, the correction factor could be altogether neglected.

Next we turn to the application of measuring the amount of permeant adsorbed by the packaging materials. Following equilibration, the package (e.g. package 45 or test samples 17, 18) is emptied of its contents and placed in chamber 10. An accumulated permeant amount in the internal space of chamber 10 will directly correspond to the amount of permeate dissolved into the packaging materials. Two types of data analyses is possible. In Method 1, the package is left in chamber 10 for a prolonged time until no further accumulation is detected. Depending on the quantity of permeant absorbed, it may be necessary to conduct one or more purge cycles if the accumulating permeant concentration meets or exceeds the high concentration limit of the sensor measurement range. The final concentration level attained multiplied by the volume in chamber 10 represents the amount of adsorbed permeant.

Figure 6:
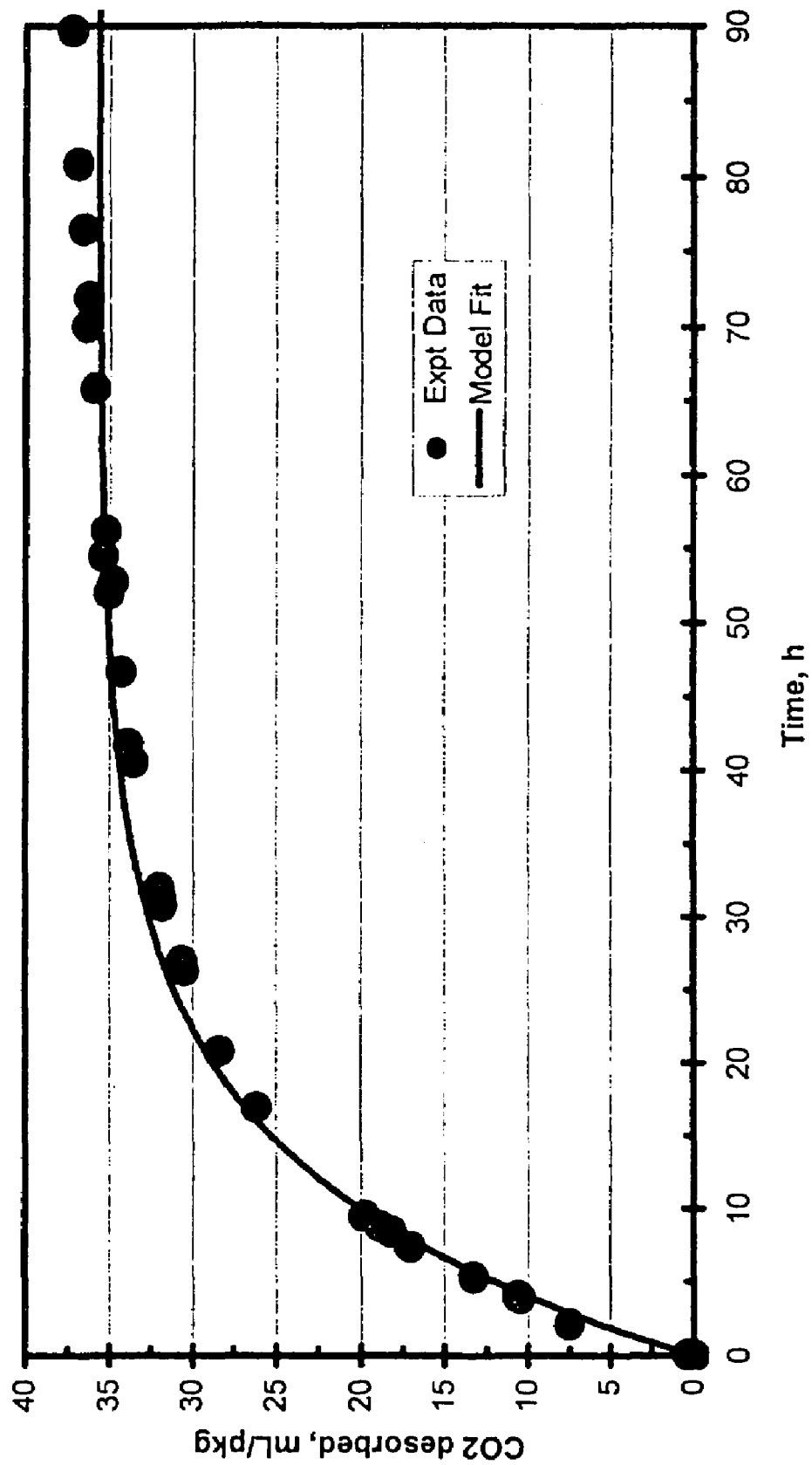
FIG. 6 is a plot of permeant desorbed and calculated as the product of the sensed concentration and the test chamber volume in a method performed in accordance with the present invention.

Results of an example of Method 1 testing are shown as a plot in FIG. 6. In this test, a carbonated soft drink bottle is emptied of its contents, rinsed with water to remove all residual carbonated water, and placed in test chamber 10. The chamber temperature is raised to 120° F. to speed up the process of desorption, and the concentration of the permeant ($CO_2$) is continuously monitored. The amount of permeant desorbed at any time is calculated as the product of the sensed concentration and the test chamber volume, and is plotted in FIG. 6. The symbols represent actual amounts calculated thus, and the solid line is a simple exponential desorption model used to fit the experimental data in order to calculate the final amount of sorbed $CO_2$ in the package.

In data analysis Method 2, the time history of concentration change can be reconciled with a mathematical model of the transient permeant diffusion process. The mathematical model consists of solving either analytically or numerically the diffusion equation for permeate diffusion in the packaging material. Permeant solubility or sorption and diffusivity parameters that best describe the experimentally observed transient permeation behavior are then estimated by any suitable algorithm.

Method 2 is preferable when the total amount of adsorbed permeant is small or when the packaging materials have good permeant barrier properties (i.e., exhibits very poor diffusion for the permeant). Under such conditions, equilibrium desorption will take an inordinately long time requiring one to measure small sensor signals against noise over very long periods. In addition, even the tiniest leaks in the chamber could produce significantly erroneous results as well as other materials used in the chamber may begin to adsorb the permeant appreciably and interfere with the test method.

A more sensitive method for measuring the solubility of permeant in the packaging materials involves equilibrating open packaging materials with the permeant under pressure in a separate container, depressurizing and flushing the open packages with an inert medium to rid them of all entrained permeant, and then testing for sorption using the method above. This approach enables loading the packaging materials with significantly larger quantities of the permeant than is possible by the conventional packaging approach because much higher pressures can be used to drive sorption. Higher levels of permeate sorption are easier to measure accurately and therefore, this method improves sensitivity. Since permeation occurs from both the inside and outside surfaces of the open package, an analytical solution for the diffusion equation is available without the need for complicated numerical algorithms resulting in a very robust process for measuring sorption.

Figure 4:
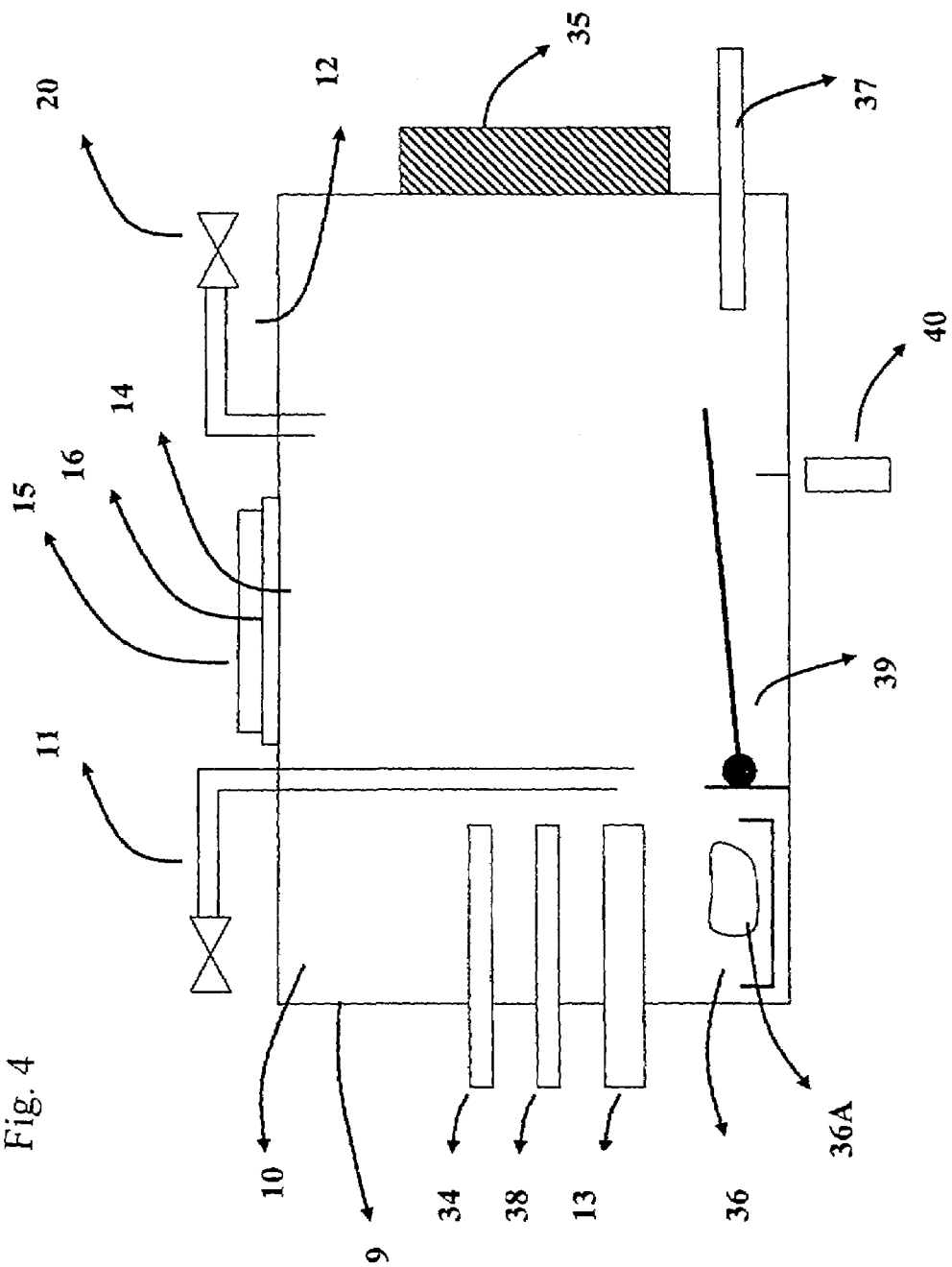
FIG. 4 is a semi-schematic diagram illustrating optional agitation, temperature and relative humidity control apparatus, in accordance with the present invention.

Next we turn to the preferred procedures for controlling the test conditions (temperature and relative humidity) for applications where such special controls are required. If the test can be conducted in a controlled environment room, it is unlikely that the following design modifications would be needed except when sensor 13 produces enough heat to appreciably change the temperature in test chamber 10. Nevertheless, the following specifications describe a preferred embodiment. Attention is drawn to FIG. 4 in which some additional modifications to chamber 10 of FIG. 1 are shown in a semi-schematic drawing. A temperature sensor 34 measures the temperature in chamber 10. Ideally, this would be a resistance thermometer or a thermistor, but thermocouples or any other suitable elements could be employed. A heater and/or cooler element 35 adds or removes heat from the chamber as required to maintain the temperature sensed by temperature sensor 34 at the desired set point temperature. The amount of heat added or removed will be dependent on the deviation of the actual temperature from the set point temperature and is determined by any suitable algorithm that is implemented by a temperature controller. The heater and cooler could be two separate elements, but preferably are combined into a single element such as a thermoelectric or Peltier device.

The humidity in chamber 10 could be controlled in one of three ways. If the packages themselves do not transmit significant amounts of water vapor from within, the inert medium used to purge the chamber could be prehumidified to the desired level. The simplest, and perhaps most accurate method is to place a small container 36 in the chamber with a saturated solution of any suitable substance in water in the chamber. For example, moist sodium chloride (table salt) will control the humidity at near 75% relative humidity. Other salt solutions can be judiciously chosen and employed in a similar manner to achieve the desired relative humidity. Other useful examples are saturated magnesium nitrate solution controls relative humidity at 54% at about 70° F., potassium nitrate solution controls relative humidity at 95%, and lithium chloride solution controls relative humidity at 11%. Preferably, the material of construction for the salt solution container, as well as the salt solution itself will consist of inert formulations that do not absorb or emit the permeant themselves. When the permeant of interest is $CO_2$, sorption of $CO_2$ by the salt solution could be substantially eliminated by decreasing the pH of the salt solution below approximately pH 4.5 by adding sufficient appropriate quantities of a suitable acid. Even without such pH control steps, the concentration of the permeant in the chamber is usually at least 1.5 to 2 orders of magnitude lower than in the test packages. Thus the driving force for sorption into the humidity control solution is not likely to be significant compared to the quantities in the test packages themselves.

One disadvantage with using open containers of salt solutions is that as the water evaporates from the solution, "salt fingers" form that eventually creep out of the container into the outside space. The resulting salt deposits on the equipment, while being a nuisance, can corrode equipment and also interfere with other functions of the apparatus. Moreover, the surface area for vapor exchange is limited to the top liquid surface and thus somewhat reduces the efficiency of humidity control, particularly in large volume chambers.

In a different embodiment, container 36 can be replaced, supplemented, or filled with packages or small bags, designated 36A, of a saturated solution of any suitable substance. The packages or bags 36A are formed of a suitable material that allows interaction between the atmosphere within cavity 10 and the saturated solution of a suitable substance contained in bags or packages 36A. Preferably the interaction occurs without allowing the saturated solution to flow out of the bags or packages 36A into chamber 10. In a preferred embodiment bags or packages 36A are formed of a hydrophobic microporous material, made from polypropylene, polytetrafluoroethylene (Teflon™) or other suitable materials. Commercial materials such as Celgard 2500™ or GOR-TEX™, or even Tyvek™ can be employed. The pore structure of these materials is such that while they allow for relatively free water vapor diffusion into and out of the bags, the hydrophobic nature prevents the liquid phase from passing through at normal operating pressures relevant for the current application. Bags or packages 36A could be pre-filled and designated with a specific substantially constant humidity that can be achieved with that specific bag or package, e.g. taking into account the size of the bag and the amount and type of saturated salt solution contained therein. By appropriate choice of the salt, bags or packages 36A can be designed for very specific humidity, additional measuring devices may not be required. In fact, once such a humidity control method is incorporated, the test chamber may be used to calibrate humidity sensors. Also, bags or packages 36A can be easily introduced into chamber 10 and removed without causing undue cleaning problems.

Alternatively, humidification can be accomplished by ejecting droplets or a stream of water into chamber 10 with a suitable volumetric addition device 37, for example, a piezoelectric ejector. For this type of humidity control, a humidity sensor 38 is also required for sensing the prevalent humidity level relative to the desired set point. A controller will then take into account the deviation in actual humidity from the set point value and adjust the rate and amount of water injection into chamber 10 based on a suitable algorithm. Preferably, temperature sensor 34 and humidity sensor 38 are combined into a single probe. When the test packages themselves do not emit significant amounts of water vapor, it is possible to conduct the permeation tests at near the desired humidity levels if the inert gas medium used to flush the chamber is pre-humidified appropriately.

Typical package permeation rates are slow enough that molecular diffusion of the permeant is sufficient to substantially eliminate permeant concentration gradients in chamber 10. However, for packages that rapidly emit the permeant, the concentration in chamber 10 may not be uniform, and the concentration measured by sensor 13 would not truly represent permeant concentration throughout the chamber space. Under these conditions, it is desirable to agitate or stir the medium in the chamber space to substantially eliminate concentration gradients. A technique to achieve this is to have a spring-loaded movable member 39 positioned in chamber 10 that could be coupled magnetically to an external drive electromagnet 40. When electromagnet 40 is energized, movable member 39 is drawn toward electromagnet 40 causing a large movement of the medium in container 10, and when electromagnet 40 is de-energized, the tension in the spring returns movable member 39 to its original position. Such convection inside chamber 10 is sufficient to achieve good mixing. Alternatively, a turbine or a fan could be readily incorporated with due regard to their construction and material properties so that the integrity of the test chamber is not compromised.

Thus, new and improved apparatus and techniques for measuring package permeability have been disclosed. The new and improved apparatus and techniques can be used for measuring package permeability and/or measuring package permeant sorption. The new and improved apparatus and techniques for measuring package permeability and/or permeant sorption include accurate control of humidity and temperature and new and improved apparatus for more accurately controlling humidity. Also, the new and improved package permeability measuring apparatus and techniques are extremely accurate and substantially faster than prior art apparatus and techniques. Further, the new and improved package permeability measuring apparatus and techniques can be used on substantially any types, shapes, and sizes of packages.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

What is claimed is:

1. A method of measuring permeability and/or permeant sorption comprising the steps of:

providing a housing impervious to a permeant of interest and defining an inner sealable chamber having an inlet for introducing into the chamber an inert medium substantially free of the permeant of interest and an outlet for removing from the chamber the inert medium, and a sensor positioned within the sealed chamber and designed to provide signals, external of the chamber, indicative of permeant concentrations within the chamber;

placing packages to be tested in the chamber, flushing the chamber with the inert medium using the inlet and outlet to reduce permeant concentration in the chamber to a suitable low limit, and sealing the chamber subsequent to flushing;

monitoring the sensor to determine when the permeant concentration in the chamber increases to a suitable high limit; and recycling the flushing, sealing and monitoring steps a plurality of times to achieve a constant time versus permeant concentration slope between the low limit and the high limit.

2. The method of claim 1 wherein the suitable low limit is below a low sensitivity of the sensor.

3. The method of claim 1 wherein the suitable high limit is such that a partial pressure of the permeant in chamber is below a partial pressure of the permeant in the packages to be tested.

4. The method of claim 1 wherein the recycling step includes a step of recording time intervals for sensor signals to reach the high limit from the low limit and calculating a rate of permeation into the chamber from the time intervals.

5. The method of claim 1 wherein the recycling step includes periodically acquiring concentration data from the sensor signals and computing a rate of permeation using linear regression on a point-by-point basis within each measurement cycle.

6. The method of claim 1 wherein the monitoring step includes a sub-step of controlling at least one of humidity, temperature, and concentration gradients within the chamber during the monitoring step.

7. The method of claim 1 further including a step of varying temperature within the chamber during the measuring procedure according to a predetermined program to determine gross package integrity.

8. The method of claim 1 further including a step of controlling humidity in the chamber by placing a salt solution in a container incorporating a hydrophobic microporous material.

9. The method of claim 8 wherein the salt solution contained in the bag includes saturated salt and an excess of undissolved salt.

10. The method of claim 8 wherein the bag has a size and an amount and type of salt solution and excess undissolved salt contained therein calculated to maintain a selected humidity level in the chamber.

11. The method of claim 1 further including a step of controlling humidity in the chamber by providing a piezoelectric water injection device coupled to the chamber, together with a humidity sensor coupled to the chamber and a controller for determining an amount of water to be injected depending on an observed humidity level and a desired control set point.

* * * * *